(12) United States Patent
Werner et al.

(10) Patent No.: US 9,140,767 B2
(45) Date of Patent: Sep. 22, 2015

(54) ISOTROPIC METAMATERIAL LENS FOR MAGNETIC IMAGING APPLICATIONS

(75) Inventors: Douglas H. Werner, State College, PA (US); Clara R. Baleine, Orlando, FL (US)

(73) Assignees: The Penn State Research Foundation, University Park, PA (US); Lockheed Martin Corporation, Bethesda, MD (US)

( * ) Notice: Subject to any disclaimer, the term of this patent is extended or adjusted under 35 U.S.C. 154(b) by 656 days.

(21) Appl. No.: 13/462,384

(22) Filed: May 2, 2012

(65) Prior Publication Data

US 2013/0002253 A1    Jan. 3, 2013

Related U.S. Application Data

(60) Provisional application No. 61/481,524, filed on May 2, 2011.

(51) Int. Cl.
  *G01R 33/36*   (2006.01)
  *G01N 24/08*   (2006.01)
  *G01R 33/30*   (2006.01)
  *G01R 33/44*   (2006.01)

(52) U.S. Cl.
  CPC .............. *G01R 33/36* (2013.01); *G01N 24/084* (2013.01); *G01R 33/302* (2013.01); *G01R 33/441* (2013.01)

(58) Field of Classification Search
  CPC .... G01R 33/36; G01R 33/302; G01R 33/441; G01N 24/084
  See application file for complete search history.

(56) References Cited

U.S. PATENT DOCUMENTS

| | | | |
|---|---|---|---|
| 6,985,118 B2 | 1/2006 | Zarro et al. | |
| 7,365,701 B2 | 4/2008 | Sciperio | |
| 7,538,946 B2* | 5/2009 | Smith et al. | 359/569 |
| 7,623,745 B2 | 11/2009 | Podolskiy et al. | |
| 7,710,336 B2 | 5/2010 | Schweizer et al. | |
| 7,864,394 B1 | 1/2011 | Rule et al. | |
| 8,130,031 B2* | 3/2012 | Nguyen et al. | 327/565 |

(Continued)

FOREIGN PATENT DOCUMENTS

EP    2458396 A1    5/2012

OTHER PUBLICATIONS

M.J. Freire, R. Marques, L. Jelinek, "Experimental demonstration of a μ= -1 metamaterial lens for magnetic resonance imaging," *Appl. Phy. Lett.*, 93, 231108 (2008).

(Continued)

*Primary Examiner* — Dixomara Vargas
(74) *Attorney, Agent, or Firm* — Gifford, Krass, Sprinkle, Anderson & Citkowski, P.C.; Weston R. Gould

(57) ABSTRACT

Examples of the present invention include metamaterial lenses that allow enhanced resolution imaging, for example in MRI apparatus. An example metamaterial may be configured to have μ=−1 along three orthogonal axes. Superior performance was demonstrated using such improved designs, and in some examples, imaging resolution better than λ/500 was obtained. The use of one or more lumped reactive elements in a unit cell, such as one or more lumped capacitors and/or one or more lumped inductors, allowed unit cell dimensions and hence resolution to be dramatically enhanced. In some examples, a cubic unit cell was used with an essentially isotropic magnetic permeability of μ=−1 obtained at an operating electromagnetic frequency and wavelength (λ).

17 Claims, 17 Drawing Sheets

(56) References Cited

U.S. PATENT DOCUMENTS

| | | | |
|---|---|---|---|
| 8,912,973 | B2* | 12/2014 | Werner et al. ............... 343/853 |
| 2009/0096545 | A1 | 4/2009 | O'Hara et al. |
| 2009/0201221 | A1 | 8/2009 | Werner et al. |
| 2010/0097048 | A1 | 4/2010 | Werner et al. |
| 2010/0259345 | A1 | 10/2010 | Kim et al. |
| 2011/0204891 | A1* | 8/2011 | Drake et al. ............... 324/309 |
| 2011/0209110 | A1 | 8/2011 | Grbic et al. |
| 2014/0159479 | A1* | 6/2014 | Nomura et al. ............... 307/9.1 |

OTHER PUBLICATIONS

J.B. Pendry, "Negative refraction makes a perfect lens", *Phys. Rev. Letts.*, 85(18), 3966 (2000).

M.C.K. Wiltshire et al., "Microstructured Magnetic Materials for RF Flux Guides in Magnetic Resonance Imaging," *Science*, 291, 849 (2001).

M.J. Freire, R. Marques, "Planar magnetoinductive lens for three-dimensional subwavelength imaging," *Appl. Phys. Lett.*, 86, 182505 (2005).

M. Lapine, M. Jelinek, M.J. Freire, R. Marques, "Realistic metamaterial lenses: Limitations imposed by discrete structure, "*Physical Review B*, 82, 165124 (2010).

Z.H. Jiang et al., "An Isotropic 8.5 MHz Magneti mega-lens", *IEEE International Symposium on Antennas and Propagation (APSURSI)*, 1151-1154 (2011).

C.P. Scarborough, "Experimental demonstration of an isotropic metamaterial super lens with negative unity permeability at 8.5 MHz", *Applied Physics Letters*, 101(1), 2, (2012).

G. Goussetis, et al., "Periodically loaded dipole array supporting left-handed propagation," *IEE Proc.-Microw. Antennas Propag.*, vol. 152, No. 4, Aug. 2005.

\* cited by examiner

FIG. 4B
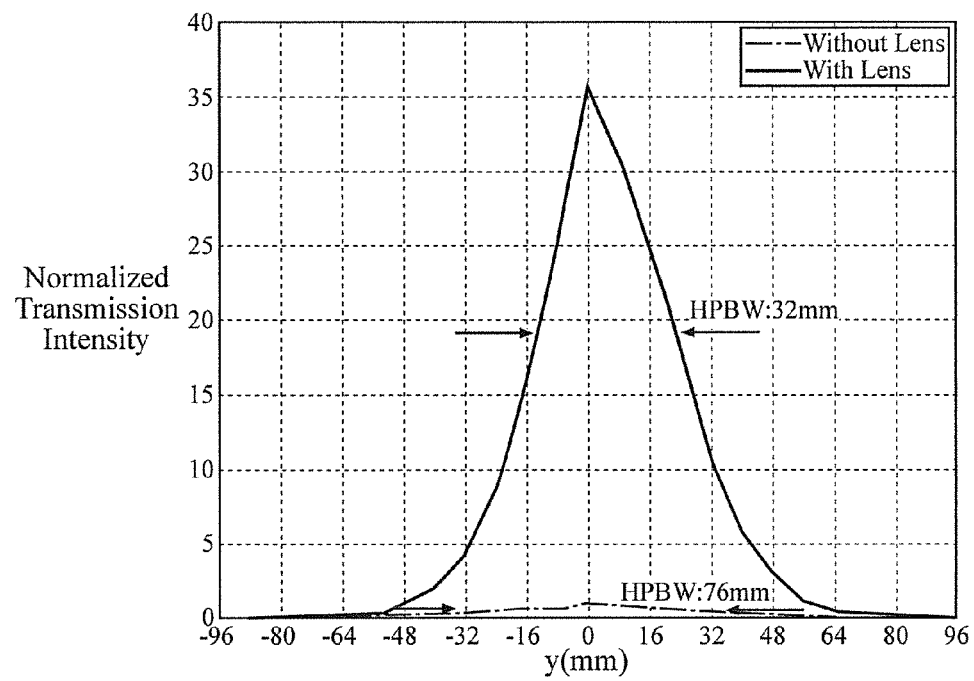
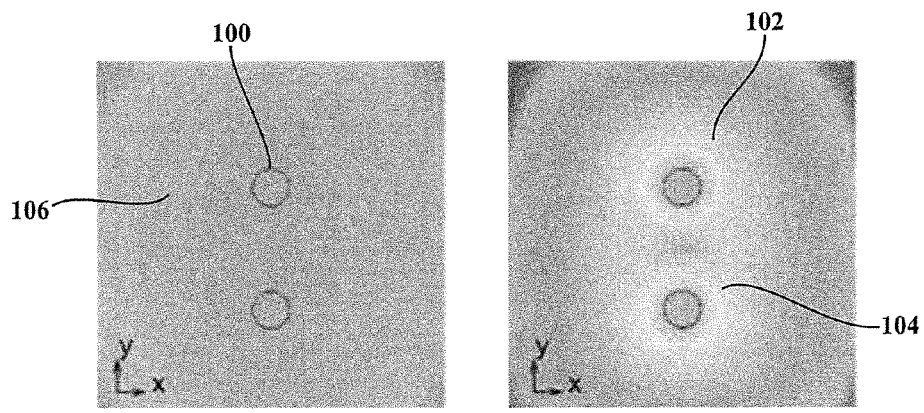
FIG. 5A        FIG. 5B

FIG. 9A  FIG. 9B  FIG. 9C

ISOTROPIC METAMATERIAL LENS FOR MAGNETIC IMAGING APPLICATIONS

REFERENCE TO RELATED APPLICATION

This Utility patent application claims priority to U.S. provisional patent application Ser. No. 61/481,524, filed May 2, 2011, the content of which is incorporated herein in its entirety.

FIELD OF THE INVENTION

The invention relates to metamaterials, including metamaterial lenses used for magnetic resonance imaging applications.

BACKGROUND OF THE INVENTION

MRI (magnetic resonance imaging) resolution can be increased by increasing the magnetic field strength, but these higher magnetic field systems are costlier, bulkier, and require additional infrastructure. Hence, it would be desirable to increase resolution without increasing the magnetic field strength. Improved methods and devices for conditioning magnetic field distributions, including imaged fields, would be useful for a variety of applications.

SUMMARY OF THE INVENTION

Examples of the present invention include metamaterials configured as 3-dimensional isotropic structures having $\mu=-1$ in the x-y-z dimensions. Such metamaterials may be used as lenses to obtain improved imaging resolution, for example in MRI apparatus. Example designs include metamaterial unit cell configuration having ring resonators with lumped capacitors. In some example, ring resonators are combined with lumped capacitors and inductors, such as meander line inductors or lumped inductors.

Effectively homogeneous and isotropic magnetic metamaterial lenses were designed with a negative unity effective permeability at an operational frequency. For proton MRI applications, the operational frequency is determined the static magnetic field, and example lenses were designed for 0.2 T (8.5 MHz) and 1.5 T (63.8 MHz) operation. Other frequencies may be determined by adjusting the capacitive and/or inductive elements used.

Exceptional low-frequency performance was achieved using both inductor-loaded and capacitor-loaded ring resonators on the faces of periodic volumetric unit cells, such as cubic unit cells, in the metamaterial was designed. An example metamaterial slab functions as a near-field magnetic lens, providing a higher resolution than is possible in free space.

Measurements of fabricated prototypes confirmed the metamaterial simulations, both in the frequency of operation and in the imaging properties of the lens. Measurements with two closely-spaced loops in the source plane demonstrated both the improved resolution and increased field strength made possible by the lens.

Example metamaterial lenses allow improved low frequency imaging applications, such as portable MRI systems.

Advantaged of the metamaterial lenses include resolution improvement in magnetic imaging. Applications also include magnetic field enhancement, for example in field concentration of a magnetic field source, and increased penetration depth for imaging. A lens may be used for enhancing and concentrating the magnetic field, which then can propagate deeper into the body. In some examples, the same lens can be used for field enhancement and for resolution enhancement of the image.

An example metamaterial lens has an isotropic magnetic permeability of $\mu=-1$ at the operating frequency of the lens, and including resonators arrayed in three orthogonal planes. Each resonator includes a conducting ring structure and a surface-mounted reactive component. The surface-mounted reactive component may be a surface-mounted inductor or surface-mounted capacitor. The metamaterial lens may include dielectric substrates (dielectric layers supporting resonators) arranged in three orthogonal planes, intersecting with each other to form an arrangement of dielectric cubes. The cubes may be hollow (air filled), the cube faces being defined by portions of dielectric substrate.

For example, a dielectric cube may have first and second opposed faces formed from first and second dielectric substrates, third and fourth faces opposed formed from third and fourth dielectric substrates, and fifth and sixth opposed faces formed from fifth and sixth dielectric substrates. The first and second dielectric substrates are parallel and spaced-apart, similarly for the third and fourth dielectric substrates and the fifth and sixth dielectric substrates. Resonators in the metamaterial lens may be generally identical. Resonators may be ring resonators formed by conducting patterns on the dielectric layers. For example, the conducting patterns may be conducting tracks, such as metal tracks, formed by etching on a dielectric substrate, for example as a printed circuit board. The surface-mounted reactive components may mounted over gaps the conducting patterns, a conducting ring with a gap therein sometime being termed a split ring resonator. Ring resonators may include at least one loop structure, for example a combination of conducting tracks and surface-mounted components forming a closed loop. The term "ring" is not limited to circular forms, but also includes generally square and other shaped patterns. A metamaterial lens may have a repeated unit cell structure, each unit cell being a cubic unit cell with resonators located at each face thereof. For example, the lens may include cubic structures in which the faces of the cube are formed by a dielectric substrate, with a resonator located each face. Each dielectric substrate may include a square or regular array of resonators, the dielectric substrates intersecting in three dimensions to give arrangements of resonators at the face of the cubic structures. In some examples, each resonator may include a surface-mounted capacitor and/or a surface-mounted inductor. In some examples, each resonator includes a surface-mounted capacitor and a meander-line inductor. An example apparatus is a metamaterial lens having an operating frequency between 1 MHz to 1 GHz, such as 5 MHz to 500 MHz, the metamaterial lens having an isotropic magnetic permeability of $-1$ at the operating frequency, the metamaterial including a plurality of resonators, each resonator including a conducting ring structure having a gap therein, and a reactive component electrically connected across the gap in the ring structure, such as an inductor or capacitor. The reactive component may be a surface mounted component, such as a capacitor or an inductor. The metamaterial may include dielectric substrates arranged parallel to three orthogonal planes and intersecting so as to form dielectric cubes, the resonators being formed on faces of the dielectric cubes.

Example apparatus include nuclear magnetic resonance apparatus, such as a magnetic resonance imaging apparatus. The apparatus may include a magnet providing a static magnetic field, wherein the operating frequency is a nuclear resonance frequency in the nuclear magnetic resonance apparatus, for example a proton magnetic resonance frequency in the static magnetic field. For example, the operating frequency may be a nuclear resonance frequency within an imaged object. A variable magnetic field generator may be used to form, e.g. field gradients for magnetic resonance imaging purposes, as known in the magnetic resonance imaging art. The image resolution of the metamaterial lens may be better (i.e. smaller) than $\lambda/100$, where is the electromagnetic wavelength at the operating frequency. The operating frequency of the apparatus may be in the range 1 MHz to 1 GHz, for example in the range 5 MHz to 500 MHz. A method of improved magnetic resonance imaging of an object in a magnetic field includes locating an isotropic metamaterial lens, such as an example lens described herein, between the object and an imaging sensor. A method of increasing MRI resolution of an imaged object in an MRI apparatus without increasing static magnetic field strength includes introducing an isotropic metamaterial lens as described herein into the MRI apparatus between the imaged object and an imaging sensor, thereby increasing MRI resolution.

BRIEF DESCRIPTION OF THE DRAWINGS

FIGS. 4A-4B show measured image profiles for a single magnetic source loop. FIG. 4A shows the measured transmission intensity from a loop in the source plane to a loop scanned along the x-axis in the image plane, and FIG. 4B shows the measured transmission intensity with the receiving loop scanned along the y-axis.

FIGS. 5A-5C shows measurements and simulations of two magnetic source loops spaced 80 mm apart. FIG. 5A shows the simulated magnetic field strength in the image plane without the metamaterial present, and the two magnetic sources cannot be resolved. FIG. 5B shows simulated magnetic field strength in the image plane with the metamaterial present, where magnetic sources appear as two distinct peaks. FIG. 5C shows the measured transmission intensity from two loops in the source plane to a loop scanned in the image plane, confirming the improved resolution and increased signal strength.

FIGS. 9A-9D illustrate design of the top and bottom split-ring resonators (SRRs).

DETAILED DESCRIPTION OF THE INVENTION

Figure 1A:
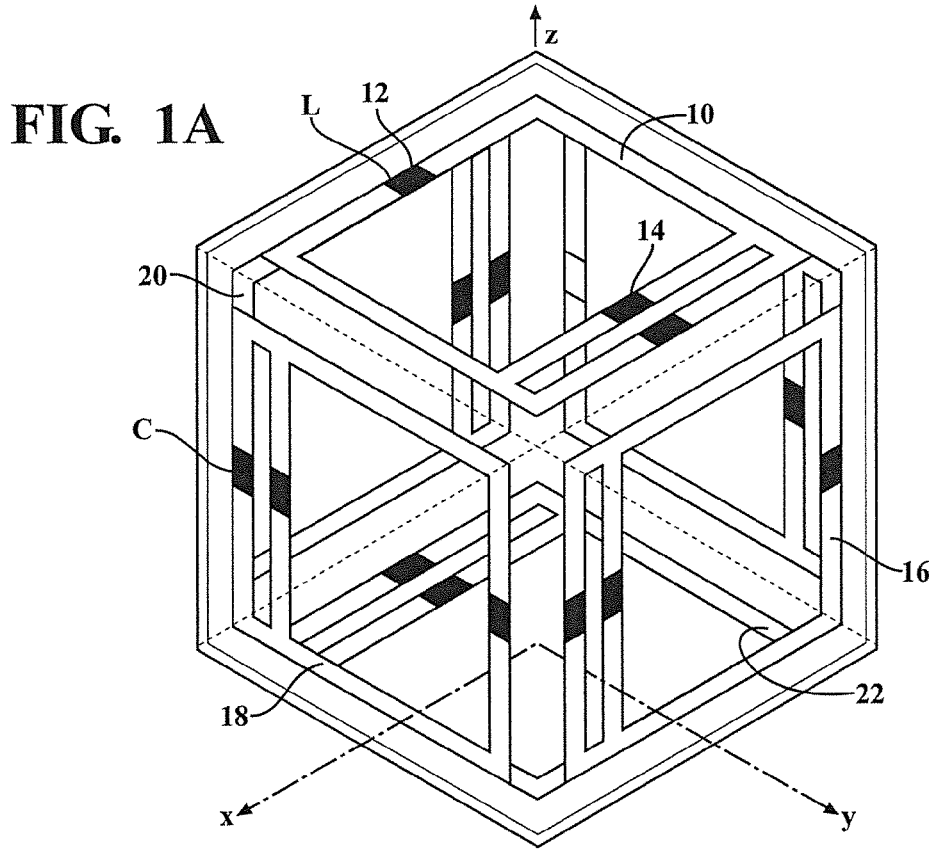
FIG. 1A shows a volumetric unit cell used in simulations.

Examples of the present invention include metamaterial lenses that allow enhanced resolution imaging, for example in MRI apparatus. An example metamaterial may be configured to have $\mu=-1$ along three orthogonal axes. Superior performance was demonstrated using such improved designs. In some examples, imaging resolution better than $\lambda/100$ is obtained, in some cases better than $\lambda/250$, such as better than $\lambda/400$, and in particular simulated examples image resolution better than $\lambda/500$ was obtained.

There is a need to increase MRI (magnetic resonance imaging) resolution without increasing the magnetic field strength. MRI resolution can be increased by increasing the magnetic field strength, but these higher magnetic field systems are costlier, bulkier, and require additional infrastructure. For instance, a 3 T MRI system costs ~$3M, while a 1.5 T MRI system costs ~$1.5M.

Example metamaterial configurations include three-dimensional (3D) isotropic metamaterials structure with $\mu=-1$ in the x-y-z dimensions. Example designs may be scaled to other frequencies of interest, for example for use in MRI apparatus of different field strengths, or for different nuclei. A 3D isotropic metamaterial lens, with engineered $\mu=-1$ in the x-y-z dimensions, may be used to focus a magnetic field down to a resolution of approximately $\lambda/500$ in the near field, and at least better than $\lambda/100$.

Examples of the present invention include essentially completely isotropic lenses, e.g. in which $\mu=-1$ in the x-y-z dimensions to a precision of greater than 1%.

Example designs include configuration using ring resonators with lumped capacitors. In some example, uses ring resonators are combined with lumped capacitors and inductors, such as meander line inductors. In some examples, split ring resonators are combined with lumped capacitors and lumped inductors. A design using split ring resonators (SRR) with lumped capacitors was modeled using a full-wave finite array simulation in HFSS and the simulation results show resolution enhancement. Resolution in the order of $\lambda/500$ was obtained, which has been achieved by a reduction in the unit cell size in our designs by at least a factor of two compared to other designs. This could potentially avoid the need for higher magnetic fields to increase the resolution of existing MRI systems, thus reducing the overall size of the MRI system.

In a magnetic resonance imaging (MRI) apparatus, the static magnetic field strength determines the frequency of operation. A lower static field strength decreases the cost of the machine and the potential impact on human beings at the expense of a reduced operating frequency. These low frequencies present a challenge to those designing metamaterials for use with MRI.

A lens with a refractive index of −1 (negative one) has been described as a perfect lens. J. B. Pendry. "Negative Refraction Makes a Perfect Lens," *Physical Review Letters*, Vol. 85, No. 18, 2000. The focal plane appears at a distance from the source that is twice the thickness of the lens, regardless of where the lens is positioned. The focusing is not due to curvature of the lens surface.

Examples of the present invention include a magnetic metamaterial for MRI applications, including MRI systems operating with a static magnetic field in the range 0.1-20 T. In particular, examples are presented for a static magnetic field of 0.2 T (corresponding to an operating frequency of 8.5 MHz and a free-space wavelength of 35.3 m), and 1.5 T. Other frequencies may be designed with appropriate scaling of reactive (capacitance or inductive values).

An isotropic metamaterial super lens with a negative unity permeability at 8.5 MHz is the lowest frequency electromagnetic metamaterial for MRI device applications to date.

Any lens that is of a comparable size to the human body or smaller falls into the magnetostatic limit, i. e. we need only consider near field effects for transverse electric (TE) polarization.

Metamaterial lenses were designed and fabricated that resolve two close sources that cannot be distinguished in free space, i.e. without the metamaterial lens present.

Lenses with a larger lateral size would restore the image information contained in larger wave vectors, thus allowing even finer resolution than that obtained.

Example 0.2 T, 8.5 MHz Metamaterial Lens

An effectively homogeneous and isotropic magnetic metamaterial was designed with a negative unity effective permeability at 8.5 MHz. The lens used inductor and capacitor-loaded ring resonators on the faces of periodic volumetric (cubic) unit cells comprising the metamaterial. A two-layer metamaterial slab functioned as a near-field magnetic lens, providing a higher resolution compared to free space imaging.

Measurements with two closely-spaced loops in the source plane demonstrated both the improved resolution and increased field strength made possible by the lens. The presented metamaterial lens allows improve low frequency imaging applications, including relatively inexpensive portable MRI systems.

An example 8.5 MHz lens was designed that measured approximately 23 cm square and 4 cm thick, which is less than 1/150 of the free-space wavelength. Creating a resonant periodic unit cell that is more than one thousand times smaller than the operating wavelength was a significant engineering challenge. The lens had two layers of a cubic unit cell with 21 mm sides containing a 17 mm square ring on each of the inner faces. Each ring was loaded with a capacitor and inductor, which lowers the resonant frequency and the frequency at which the real part of the effective permeability reaches negative one. The capacitors and inductors were mirrored with respect to the rings on either side of each circuit board to reduce any bi-anisotropic properties, which allows for the creation of an effectively isotropic metamaterial.

FIG. 1A shows an example unit cell design, each face having a resonator located thereon, the resonator including a ring resonator loaded with a single inductor on one side of the ring resonator and two parallel capacitors on the opposite side. The figure shows a cubic arrangement, with a ring structures 12 on a first face, the top face as illustrated, including an inductor 12, and capacitor 14. To correspond to fabricated examples, the simulated structure used two parallel capacitors. The other faces of the cubes have similar resonators, for example (as illustrated) resonators 16 and 18 on the closer side faces, 20 on a rear side, and 22 on the base.

The figure shows orthogonal directions labeled x,y,z, a resonator being located on each face of a cube. In a fabricated device, dielectric substrates may be arranged in three sets, each set of substrates being spaced-apart, where first, second and third sets of dielectric substrates are arranged parallel to first, second, and third orthogonal planes (e.g. xy, yz, and xz planes as illustrated), respectively.

In fabricated examples, the ring structure is a conducting pattern, and may be formed as a metal track on a dielectric substrate, for example using printed circuit board (PCB) techniques. The surface-mounted reactive components are mounted across gaps in the conducting track, for example by soldering the component at each end to end portions of the track each side of the gap. For example, interlocking dielectric substrates may be used to form a cube of dielectric material, each face of the cube supporting a resonator.

Figure 1B:
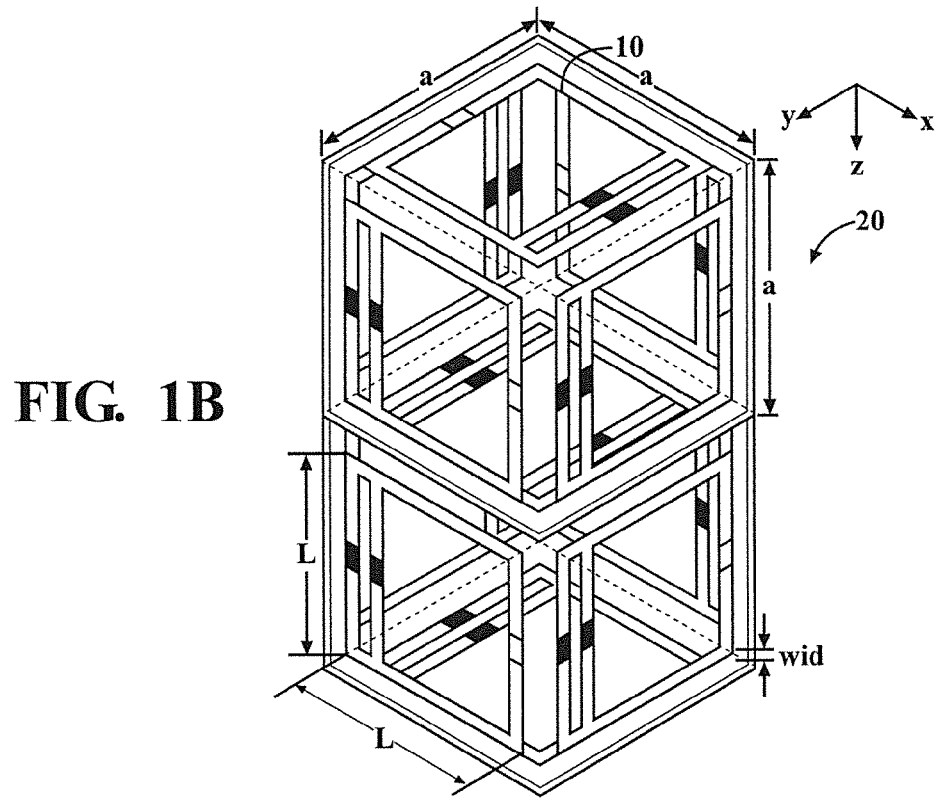
FIG. 1B shows a two-layer configuration.

FIG. 1B shows a two-layer unit cell 20 used in lens simulations, where ring resonators (such as resonator 10) on opposite faces of the cube may be mirrored to reduce bianisotropy. The unit cell dimensions were: periodicity a=21 mm; ring side length L=17 mm, trace width wid=1.2 mm; dielectric material was FR4, dielectric thickness was 0.02 inches, lumped capacitors C=2200 pF, lumped inductors L=27 nH. Here, each layer has the thickness of a cube such as shown in FIG. 1A, or a mirrored or other analogous version thereof.

Through simulation, the frequency at which $\mu = -1$ was found to scale as $(LC)^{-0.5}$. This relationship can be used to adjust the values of reactance to obtained a desired resonance frequency. An improved method of designing a metamaterial lens includes modeling a lens having arbitrary reactive values, determining the frequency at which $\mu = -1$, and then scaling the reactive values to obtain $\mu = -1$ at a desired operating frequency.

The two-layered unit cell of FIG. 1B, with periodic boundary conditions in the x-y plane and Floquet ports on the top and bottom surfaces, was simulated using the full-wave electromagnetic modeling package Ansoft HFSS™ (Ansys, Inc., Canonsburg, Pa.). Simulated reflection and transmission coefficients (S-parameters) were used to retrieve the effective electromagnetic properties based on a standard inversion method. Tuning the capacitance, inductance, and various dimensions allowed the $\mu = -1$ frequency to be adjusted for operation at 8.5 MHz, using an inductance of 27 nH and a total capacitance of 4,400 pF, split between two parallel 2,200 pF capacitors.

Figure 2A:
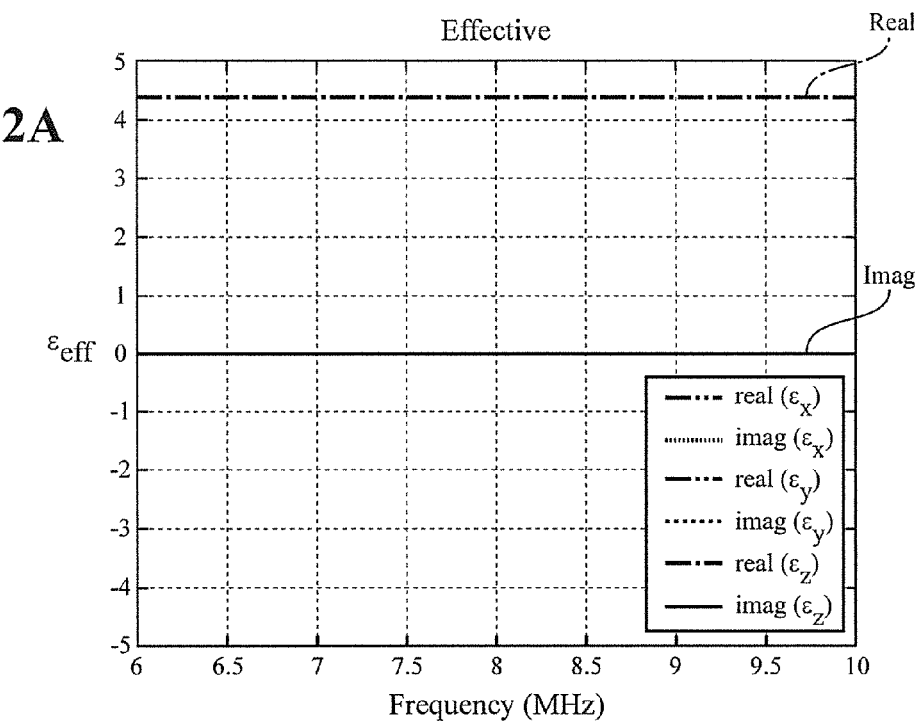
FIGS. 2A-2B show the simulated effective permittivity and effective permeability of a metamaterial lens, where the real part of the dispersive permeability passes through negative 1 at 8.5 MHz with very low loss.
Figure 2B:
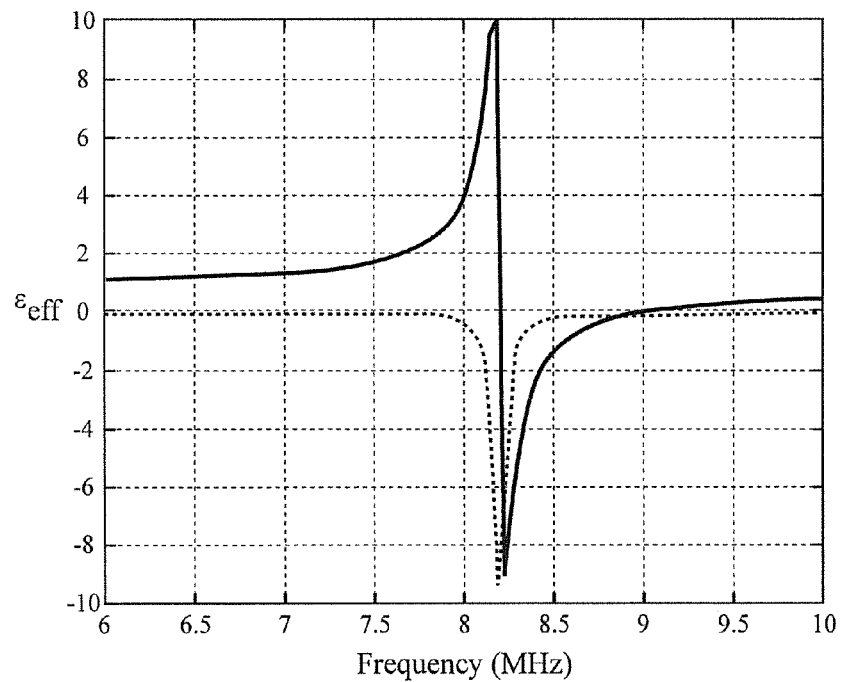

FIG. 2A shows the effective real permittivity retrieved from unit cell simulations is non-dispersive with a value close to 4 (higher than that of free space), while the effective permeability shown in FIG. 2B shows a Lorentzian type of response with a resonance around 8.2 MHz. The imaginary part of $\mu$ is in the vicinity of −0.13 at the desired operating frequency of 8.5 MHz, which is also where the real part of the permeability reaches −1. As a result, the absorption loss is nearly negligible. The properties of all three dimensions were simulated and these traces are overlaid, showing that they are essentially identical and the lens is isotropic. The track thickness had a minor effect, as illustrated.

To validate the magnetic properties, a planar square lens was fabricated with 11 by 11 unit cells and two layers thick. The effective properties retrieved from the unit cell simulations were used to model an appropriately sized homogeneous slab. Small loop probes of approximate radii 13 mm were employed as magnetic sources placed above the lens at a distance equal to half of its thickness. The loop probes provide an approximate measure of the magnetic field, and the measurements are expressed in terms of transmitted power, which corresponds to the square of the magnetic field.

Figure 3A:
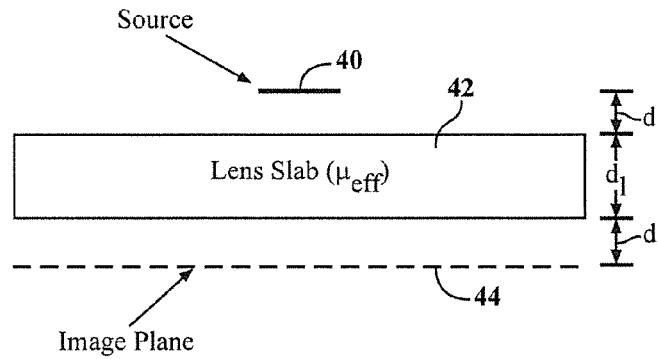
FIG. 3A shows a schematic of the imaging configuration.

FIG. 3A schematically shows show a lens slab 40, considered as an ideal lens with effective permeability found from unit cell simulation. A source 40 is located a distance d from the lens, with lens thickness $d_1$, and the image plane 44 is located at a distance d from the opposite face of the lens.

Figure 3B:
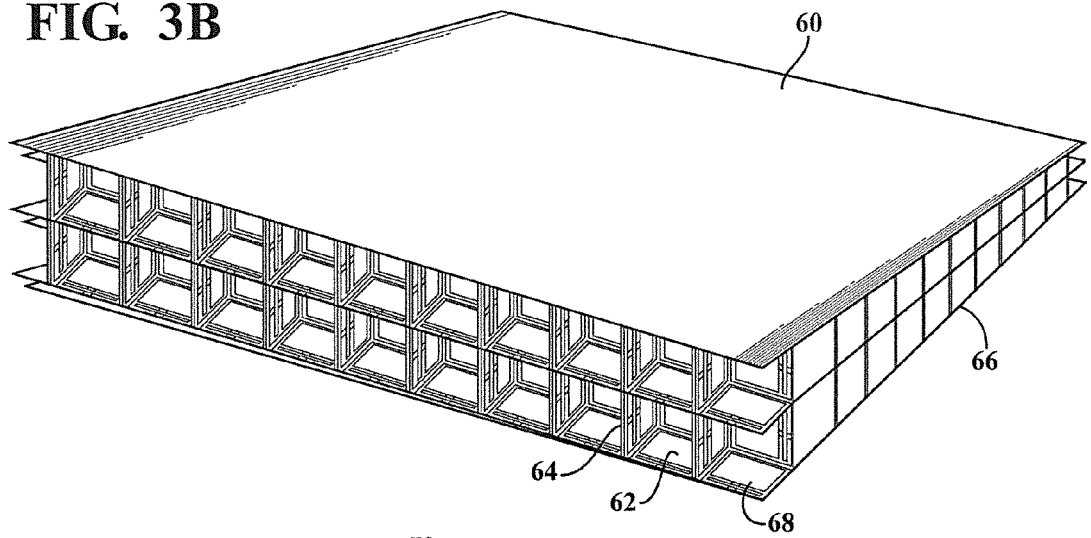
FIG. 3B shows a fabricated lens.

FIG. 3B shows a photograph of an assembled metamaterial lens. The lens includes first and second parallel and spaced-apart dielectric substrates (60 and 62), each supporting a two-dimensional array of resonators and forming the lens faces. One or more similar dielectric substrates are regularly spaced between the lens faces, forming a first set of spaced-apart dielectric substrates, each parallel to (or forming) the lens faces. Here, a single dielectric substrate is shown between the two that form the lens faces, but this is not limiting. A second set of parallel, spaced-apart dielectric substrates (such as 64) are used to support arrays of resonators in spaced-apart planes orthogonal to the lens faces. A third set of parallel, spaced-apart dielectric strips (such as 66) support arrays of resonators in spaced-apart planes orthogonal to both the lens faces and the second set of dielectric substrates.

As illustrated, the resonators (such as resonator 68) are on the inner surface of the dielectric substrates, so that the lens faces are formed by dielectric substrates. In this example, the exterior of the lens faces are dielectric surfaces. Between the dielectric substrates that form the lens faces are two sets of interlocking orthogonal dielectric substrates. Component tolerances used were 1% for capacitors and 2% for inductors. In other examples. In some examples, the capacitors may ceramic capacitors such as NP0 capacitors. In some examples, the inductors may be wirewound inductors.

Measurements of the prototype confirmed its best performance at 8.5 MHz, the exact frequency at which the unit cell simulations predicted the real part of the effective magnetic permeability to be $-1$. Simulations predicted two primary advantages afforded by the presence of the lens: improved resolution and increased magnetic field strength.

Figure 3C:
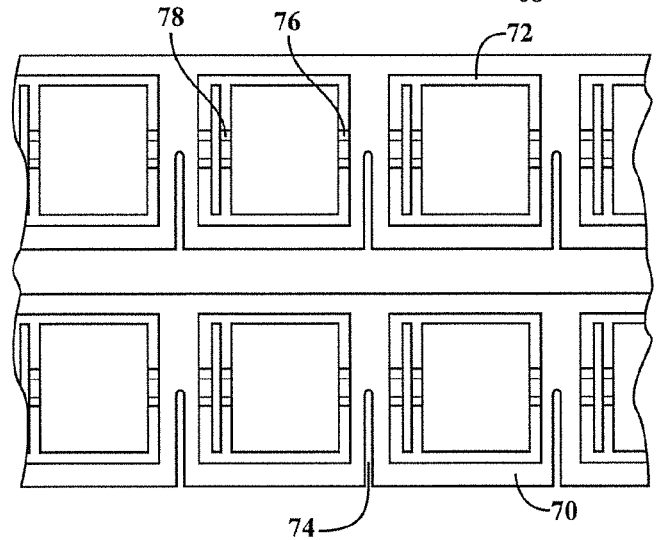
FIG. 3C-3D show portions of dielectric substrates (here, printed circuit boards) supporting resonators with surface-mounted components.

FIG. 3C shows dielectric substrates in the form of printed circuit board strips 70 with ring resonators 72 with lumped capacitors 78 and lumped inductors 76. The PCB has slots 74, facilitating an egg-crate assembly of the lens. In experiments, these substrates were used to form resonator arrays orthogonal to the lens surface.

Figure 3D:
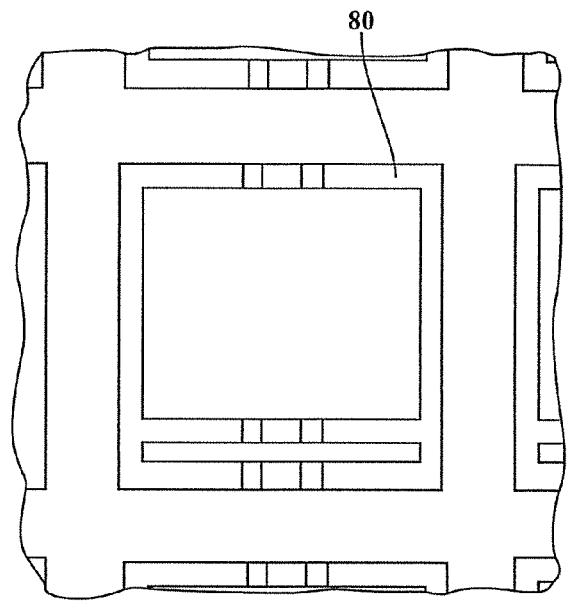

FIG. 3D shows a fabricated ring resonator 80, as part of an array on a PCB.

Figure 4A:
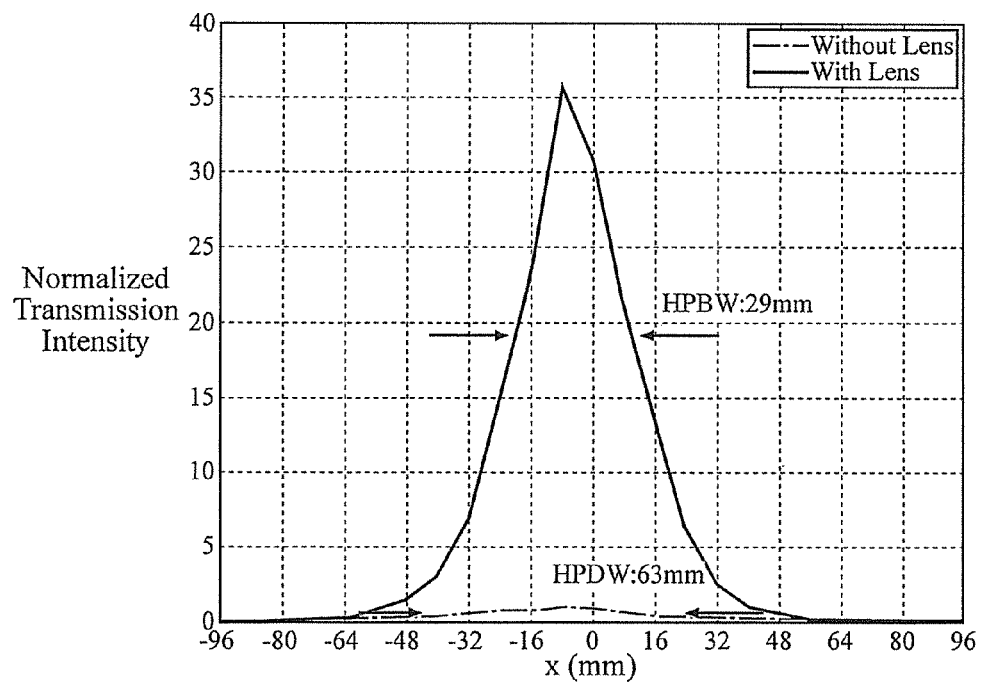

FIGS. 4A-4B show the measured transmitted power in the image plane, as a function of x and y both with and without the lens present. The transmitted power is normalized so that unity corresponds to the peak value without the lens present. The lens increased the power at the receiving loop by a factor of more than 35.

The lens improves the half-power beamwidth from 63 mm to 29 mm in the x direction, and from 76 mm to 32 mm in the y direction. These values agree quite well with those predicted by the simulations, which showed an improvement from 59 mm to 26 mm. This agreement confirms that our metamaterial design provides a good implementation of an effective negative unity permeability near-field lens. A larger lens would improve the performance further, as the lens described is electromagnetically miniscule at less than one hundredth of a wavelength square. Moreover, a thicker lens would enhance the evanescent fields even more, providing a larger detection depth than what the current prototype achieves.

Figure 5C:
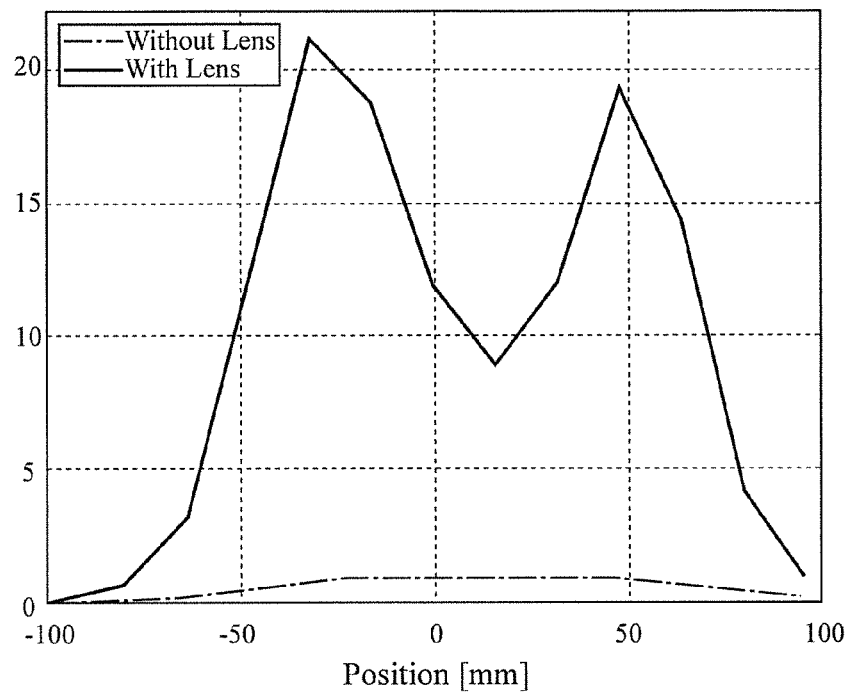

FIGS. 5A-5C show simulations and measurements with two loops in the source plane, separated from each other by 80 mm (1/444 wavelength). In FIG. 5A, the fields from the two sources (shown as rings 100) appear as a single region of imaged magnetic field (field region 106), while in FIG. 5B the metamaterial resolves the imaged fields into two distinct peaks corresponding to the two sources, as shown by regions 102 and 104. FIG. 5C compares the normalized measured transmitted power received in the image plane with and without the metamaterial present. As clearly shown in FIG. 5C, the isotropic metamaterial lens provides dramatic improvements in both imaged field strength and resolution, over imaging with no lens used.

Design of 1.5 T MRI Lens

Figure 6A:
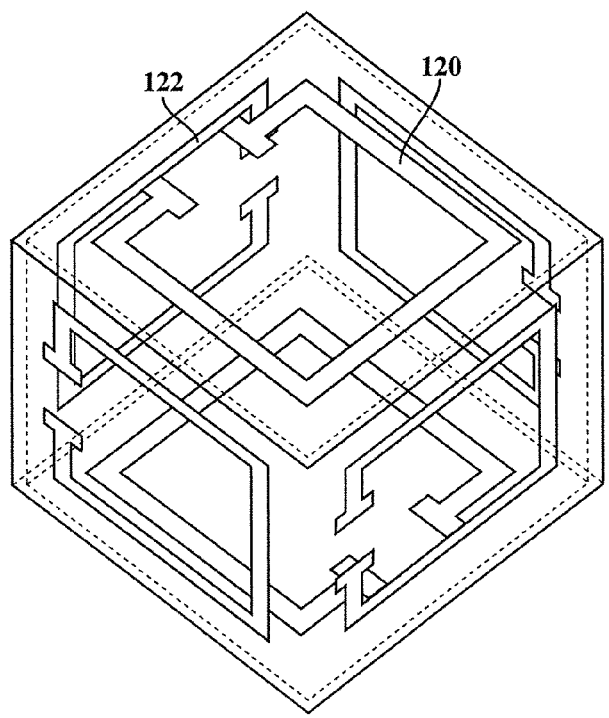
FIGS. 6A-6C shows an isotropic metamaterial lens for 1.5 T magnetic resonance imaging (MRI) using lumped capacitors.
Figure 6B:
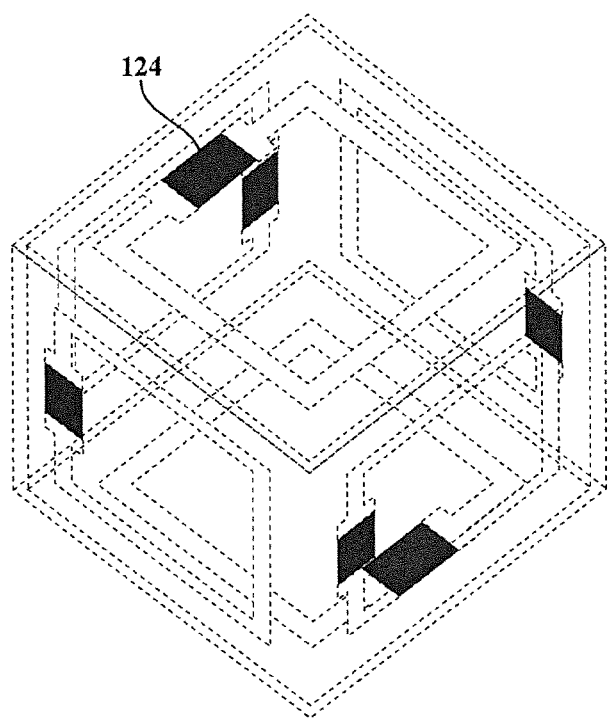
Figure 6C:
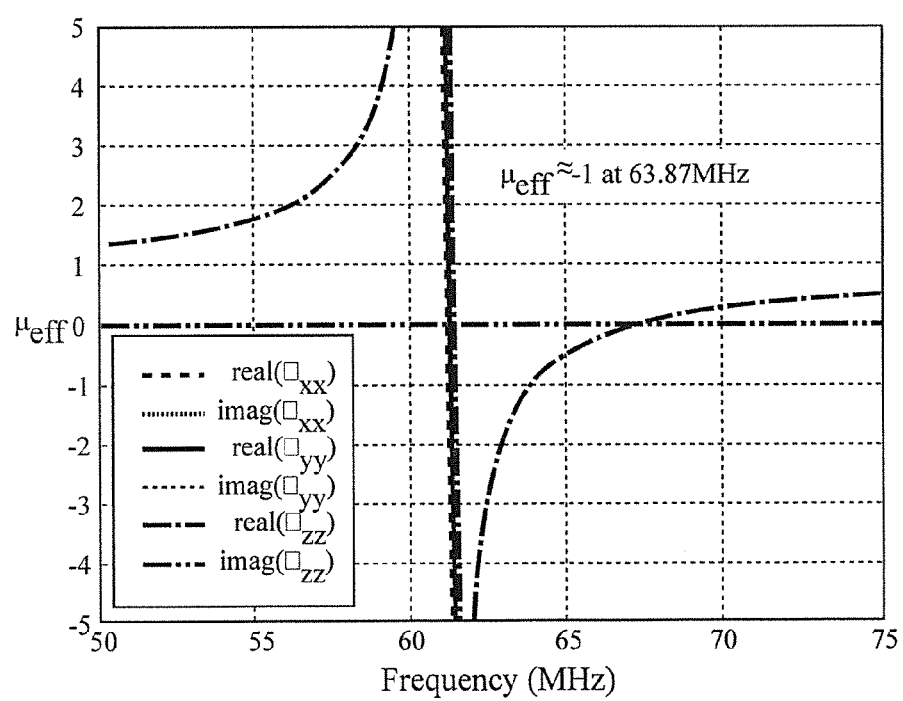

FIGS. 6A-6C show an isotropic metamaterial lens for 1.5 T MRI. This design includes rings (shown in FIG. 6A) with lumped capacitors (locations shown in FIG. 6B). The isotropic unit cell design had the following parameters: unit cell size of 8 mm×8 mm×8 mm, dielectric thickness of 0.254 mm; dielectric material is Rogers RO3035 (Rogers Corp, Chandler, Ariz.); rings are printed on the inner faces of the dielectric, lumped capacitors are 330 pF; and capacitor dimensions are the 0603 surface mount format (1.6 mm×0.8 mm×0.4 mm).

FIG. 6A illustrates the resonator structure, including a square ring resonator 120. The term ring resonator describes conducting patterns including at least one loop structure, which may be circular, square, or other form A loop structure may include capacitive gaps, e.g. over which surface-mounted reactive components are mounted. This example ring resonator has conducting elements arranged in a square pattern, which optionally has rounded corners. FIG. 6A shows ring resonators disposed parallel to three orthogonal planes, two spaced-apart resonators per plane corresponding to resonators on the opposed faces of the illustrated cube. Here, each ring resonators has a gap in the conducting pattern. FIG. 6B shows the locations of the lumped capacitors as rectangular patches (124), which correspond to mounting across the gap. Commercially available capacitors may be used. At the modeled frequency, commercially available components may be used in all example designs. FIG. 6C shows the frequency response of a metamaterial using this unit cell configuration. The real permeability was approximately $-1$ near 64 MHz for all three dimensions, and the imaginary component was minimal suggesting low loss operation.

Figure 7A:
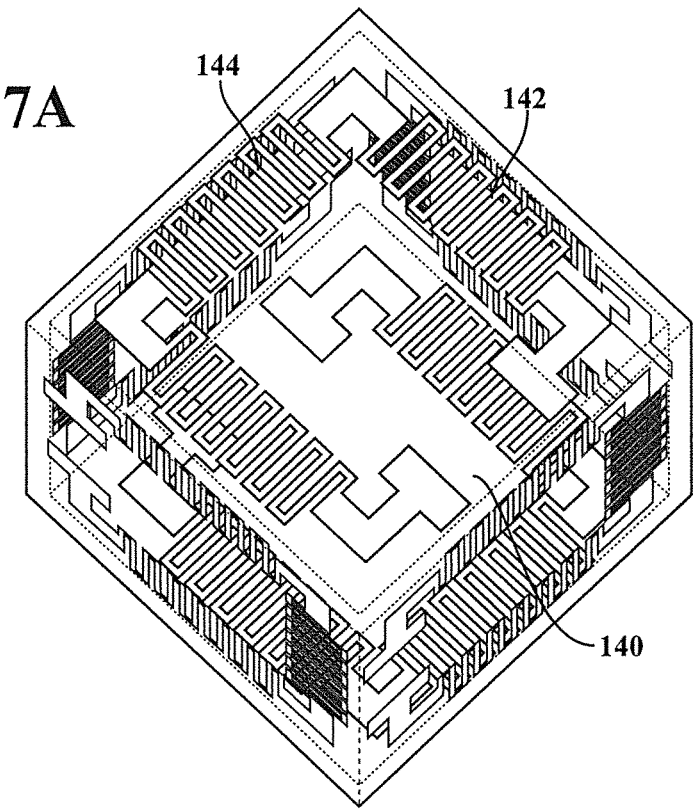
FIGS. 7A-7C show an isotropic metamaterial lens for 1.5 T MRI using a meander line inductor and lumped capacitor.
Figure 7B:
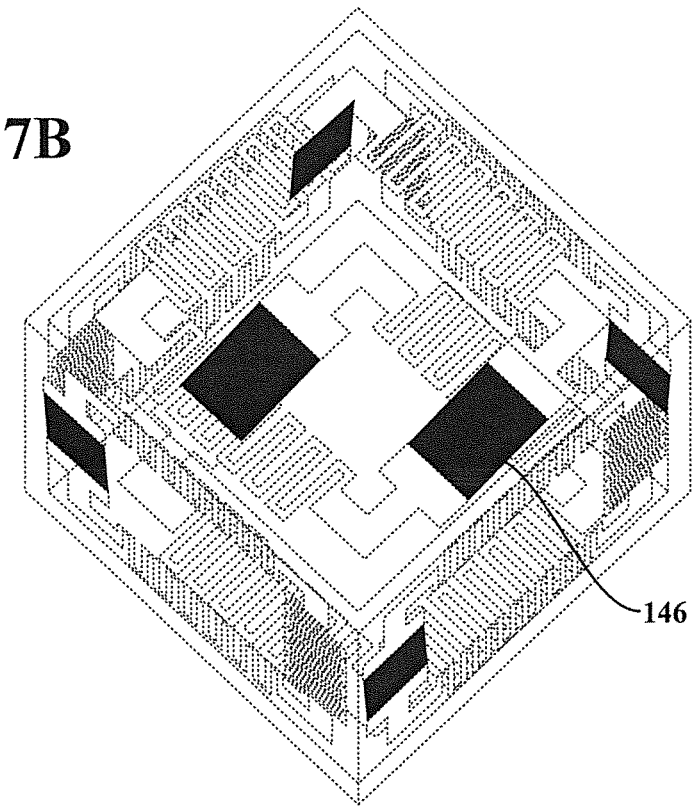
Figure 7C:
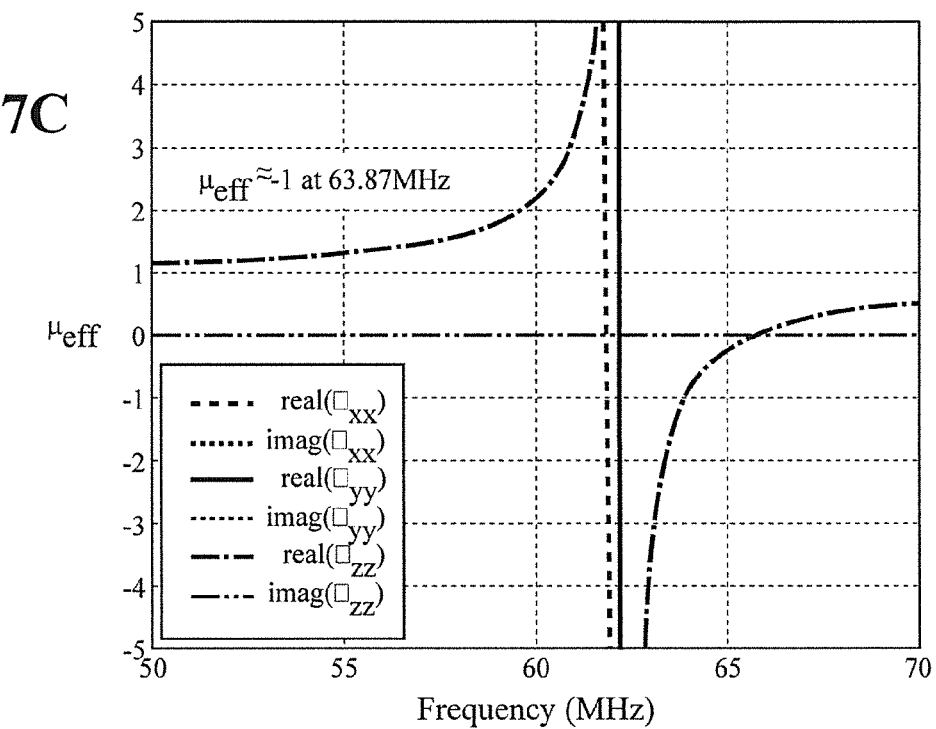

FIGS. 7A-7C shows an example isotropic metamaterial lens and properties for 1.5 T MRI. The example design includes rings with lumped capacitors (146 shows the location across gap 140) and meander line inductors (e.g. 142 and 144). In this example, the ring resonators included three meander line inductors and a surface-mounted capacitor. Commercially available components may be used. The isotropic unit cell design had the following parameters: unit cell size of 6.5 mm×6.5 mm×6.5 mm; dielectric thickness of 0.254 mm; dielectric material is Rogers RO3035; rings are printed on the inner faces of the dielectric cube; lumped capacitors are 330 pF; and the capacitor dimension is the 0603 format (1.6 mm×0.8 mm×0.4 mm).

FIG. 7A shows the rings with meander line inductors 142 and 144. FIG. 7B shows locations of lumped capacitors 146, mounted across gaps 140. FIG. 7C shows the frequency response of a metamaterial using this unit cell configuration, with excellent isotropic performance. Real permeability of $-1$ was obtained at 63.87 MHz.

Figure 8A:
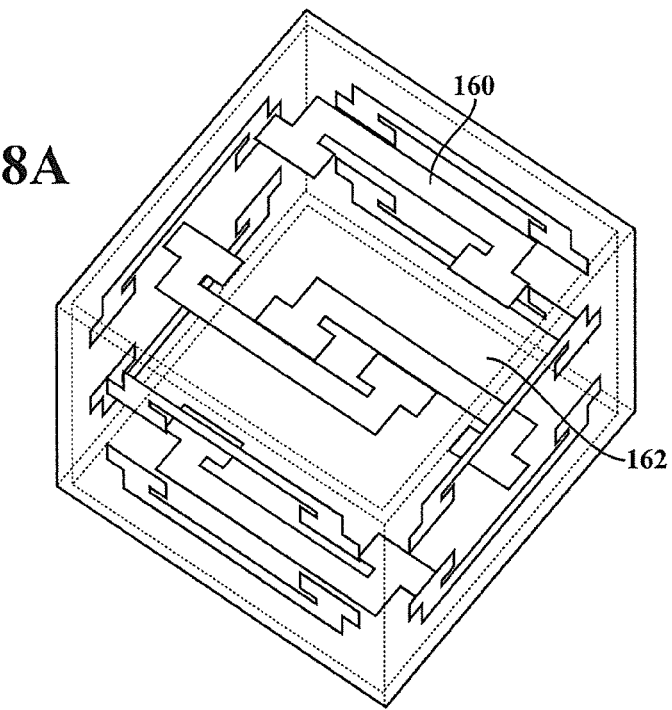
FIGS. 8A-8C show an isotropic metamaterial lens for 1.5 T MRI using lumped capacitors and lumped inductors.
Figure 8B:
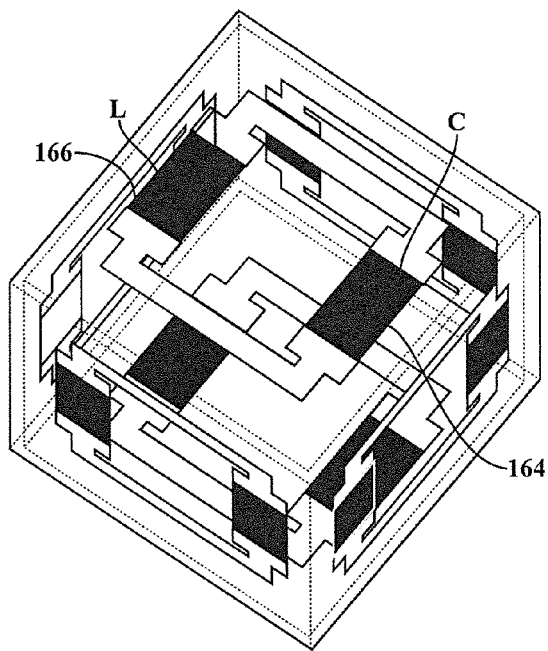
Figure 8C:
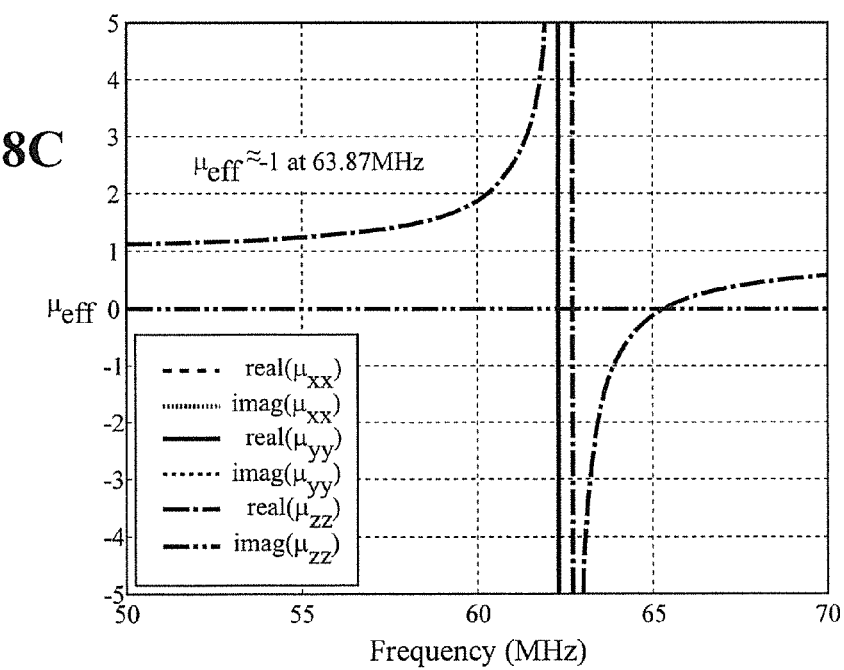

FIGS. 8A-8C show isotropic metamaterial lens for 1.5 T MRI. This example design uses split rings with both lumped capacitors 164 and lumped inductors 166 across gaps (e.g. 162) in resonators 160. Commercially available components may be used. The isotropic unit cell design included the following parameters: unit cell size of 5 mm×5 mm×5 mm; dielectric thickness is 0.254 mm; dielectric material is Rogers RO3035; rings are printed on the inner faces of the dielectric; lumped capacitors: 330 pF (commercially available); capacitor dimension is 0603 (1.6 mm×0.8 mm×0.4 mm); lumped capacitors are 10 nH (commercially available); capacitor dimension: 0603 (1.6 mm×0.8 mm×0.4 mm). FIG. 8A shows the configuration of the split rings. FIG. 8B shows the locations of lumped elements, including surface mount inductors (L) and surface mount capacitors (C). FIG. 8C shows the frequency response of a metamaterial using this unit cell configuration.

Table I below shows a comparison between the three examples discussed above and a SOA published design. The table shows data from M. J. Freire, R. Marques, and L. Jelinek, "Experimental demonstration of a metamaterial lens for magnetic resonance imaging," *Appl. Phy. Lett.*, 93, 231108, (2008), indicated as Ref. 1 in the table, Design 1 (rings with lumped capacitors, FIGS. 6A-6C), Design 2 (ring with capacitors and meander line inductors, FIGS. 7A-7C), and Design 3 (split rings with lumped capacitors and lumped inductors, FIGS. 8A-8C).

TABLE I

| | Unit Cell Size | One layer Thickness | Overall Thickness | Capacitor Value | Inductor Value | Resolution | Loss ($|\mu''|$) | FOM ($|\mu'/\mu''|$) |
|---|---|---|---|---|---|---|---|---|
| Ref. [1] | 15 mm | 15 mm | 3 cm (2 layer) | 470 pF | — | 21.2 mm | 0.04 | 25 |
| Design 1 | 8 mm | 8 mm | 3.2 cm (4 layer) | 330 pF | — | 11.31 mm | 0.03 | 33 |
| Design 2 | 6.5 mm | 6.5 mm | 3.25 cm (5 layer) | 330 pF | — | 9.19 mm | 0.04 | 25 |
| Design 3 | 5 mm | 5 mm | 3 cm (6 layer) | 330 pF | 10 nH | 7.07 mm | 0.05 | 20.2 |

Table I above compares three example designs and the design presented in Ref 1, Freire et al. Operation of negative refractive index lenses is further discussed by Pendry, Phys. Rev. Letts., 85(18), p. 3966 (2000), including operation in the magnetostatic limit. The novel designs have demonstrated superior performance (2-3× improvement) over the design of Ref. 1 (which also describes MRI configurations which may be adapted for use with examples of the present invention). Example metamaterials may operate at low frequencies for which the magnetostatic limit is applicable.

The example designs allow the dimensions of the unit cell to be reduced, for example to a layer thickness of less than 10 mm, such as 8 mm or less, and in particular to 5 mm or less. For example, the layer thickness may be in the range 3 mm-8 mm at this frequency. For cubic unit cells, the unit cell size in three dimensions may be equal to a single layer thickness.

The example designs also allow resolution to be enhanced, in a manner similar to the reduction in unit cell parameters. For example, resolution may be 12 mm or less, in particular 8 mm or less. A common approach to increase the resolution is to increase the magnetic field strength, but higher magnetic field systems are more costly, bulkier, and require additional infrastructure. Examples of the present invention allow resolution improvements without changing magnetic field strength. However, design parameters of example designs can be scaled to other (e.g. higher) field strengths if desired, allowing further resolution improvements. For example, a dimensionless parameter may be defined in terms of a ratio of wavelength and resolution (or layer thickness, or unit cell parameter) and improved along the lines given above over a range of frequencies, e.g. in the range 500 kHz-10 GHz, such as 1 MHz-1 GHz. These examples are non-limiting.

In a conventional approach, self-inductance of resonators may be used to provide the inductive component of the resonator structure. However, this limits the minimum size of the resonator. By including inductive elements into the unit cell configuration such as meander line inductors or coil inductors (which may be printed or surface-mounted inductors, or any other suitable configuration) the unit cell dimension may be appreciably reduced (as illustrated in the table above), with corresponding increases in resolution. This indicates that the inclusion of lumped inductors or other inductive elements is not a routine variation, in view of the dramatic improvements in resolution obtained. For example, a novel design including both lumped capacitors and lumped inductors allows the layer thickness to be reduced from 15 mm to 5 mm, a dramatic improvement. In some examples, components may be printed, surface-mounted, or otherwise attached to one or both sides of a dielectric substrate, such as a printed circuit board.

For example, using a proton resonance frequency of 63.87 MHz, the wavelength is 4697 mm, and the unit cell parameter for the third example is less than $\lambda/900$, whereas the referenced structure has a unit cell parameter of only approximately $\lambda/300$. Examples of the present invention include metamaterials in which the unit cell parameter and/or single layer thickness is less than $\lambda/500$. This allows dramatic increases in resolution without need to increase the magnetic field.

Example Design Process

An approach to isotropic metamaterial lens engineering is now described. This may include configuring a single unit cell firstly by designing resonators on top and bottom planes (relative to the metamaterial lens faces), and then adding four vertical SRRs identical to the top and bottom ones (so that a cubic metamaterial element has 6 identical resonators on its faces). Simulations may neglect dielectric layers, which are preferably low loss dielectric substrates. The design parameters, $\mu=-1$ in the x-y-z dimensions, may be achieved essentially exactly (within modeling or fabrication errors) for a desired frequency. Lens properties may then be estimated using the properties of a dielectric slab having these design parameters.

Figure 9D:
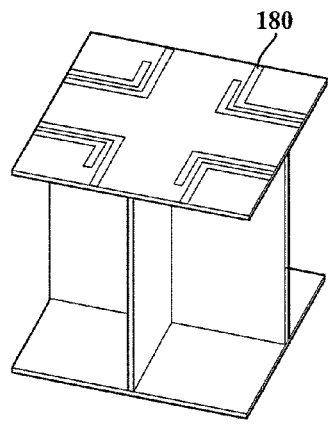
Figure 9D:
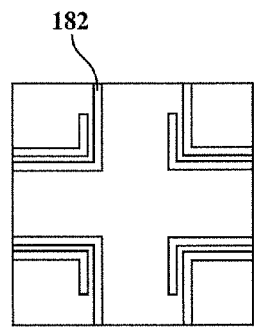
Figure 9D:
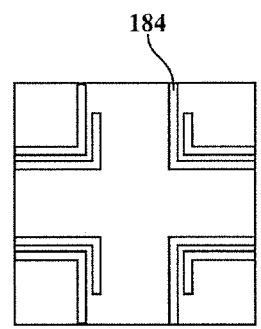
Figure 9D:
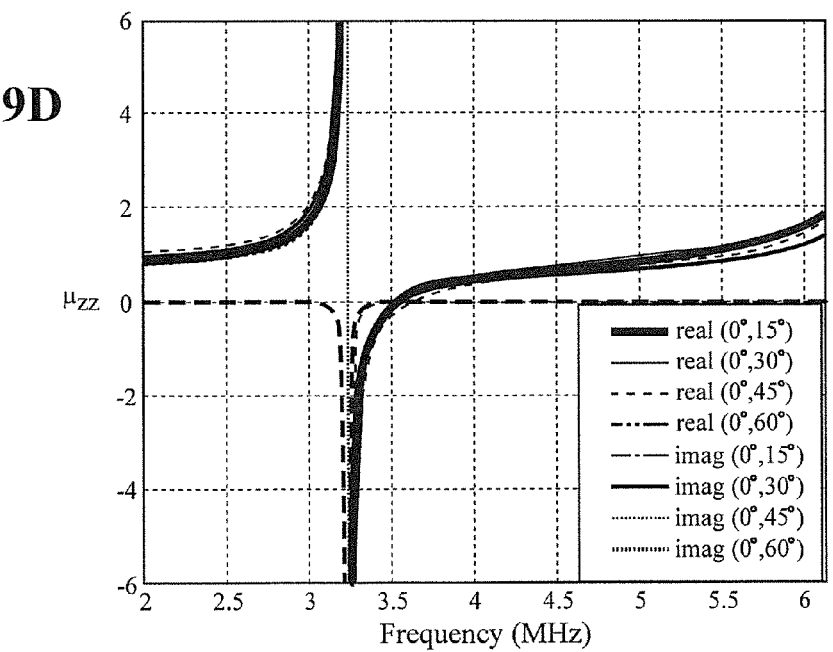

FIGS. 9A-9D illustrate design of the top and bottom SRRs, with angular response considered using an anisotropic retrieval method. FIG. 9A shows a 3D view of the unit cell, with conducting tracks 180. FIGS. 9B and 9C show top and bottom views of the unit cell respectively, conducting tracks 182 and 184 being formed on a dielectric substrate. FIG. 9D shows the frequency response of a metamaterial using the unit cell configuration after design of the top and bottom SRRs.

Table II below shows retrieved effective $\mu_{zz}$ values (with no capacitors added at this stage) at 3.4 GHz.

TABLE II

| Angle | 15° | 30° | 45° | 60° |
|---|---|---|---|---|
| real($\mu_{zz}$) | −0.98 | −0.99 | −0.99 | −1.00 |
| imag($\mu_{zz}$) | −0.08 | −0.08 | −0.07 | −0.09 |

Figure 10A:
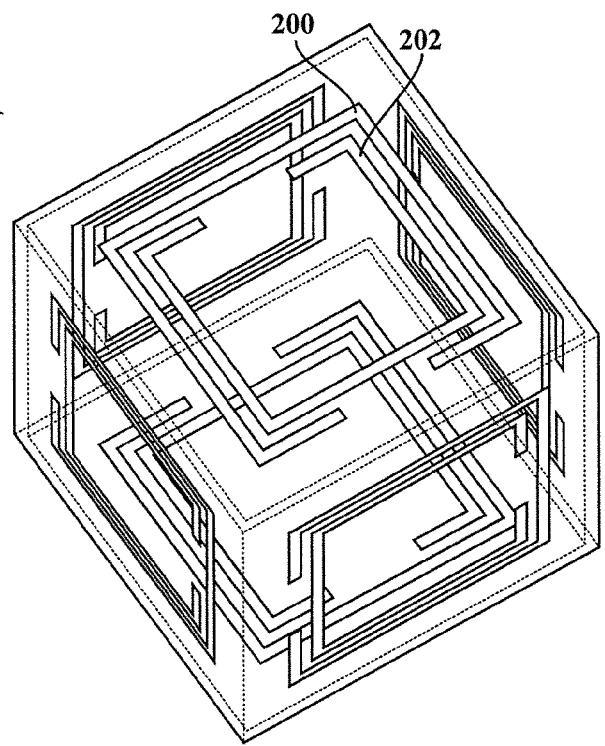
FIG. 10A-10C further illustrate the design process, adding four vertical SRRs identical to the top and bottom ones discussed in relation to FIGS. 9A-4D.
Figure 10B:
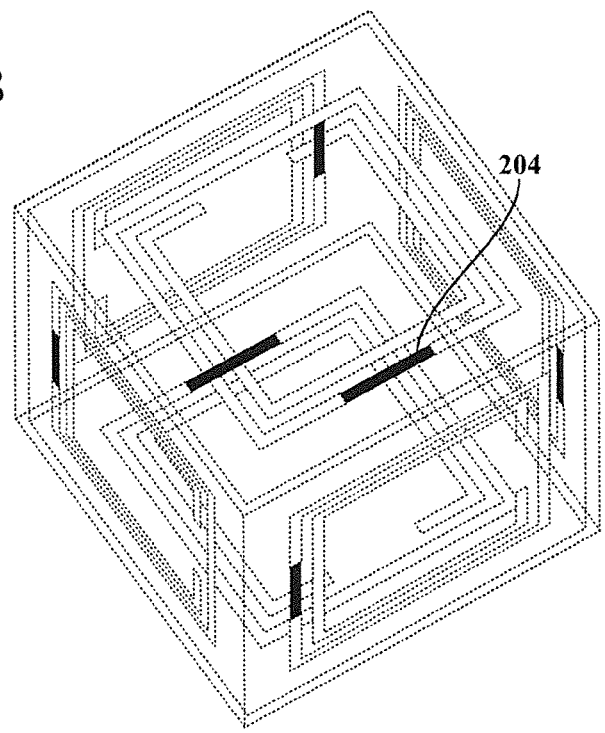
Figure 10C:
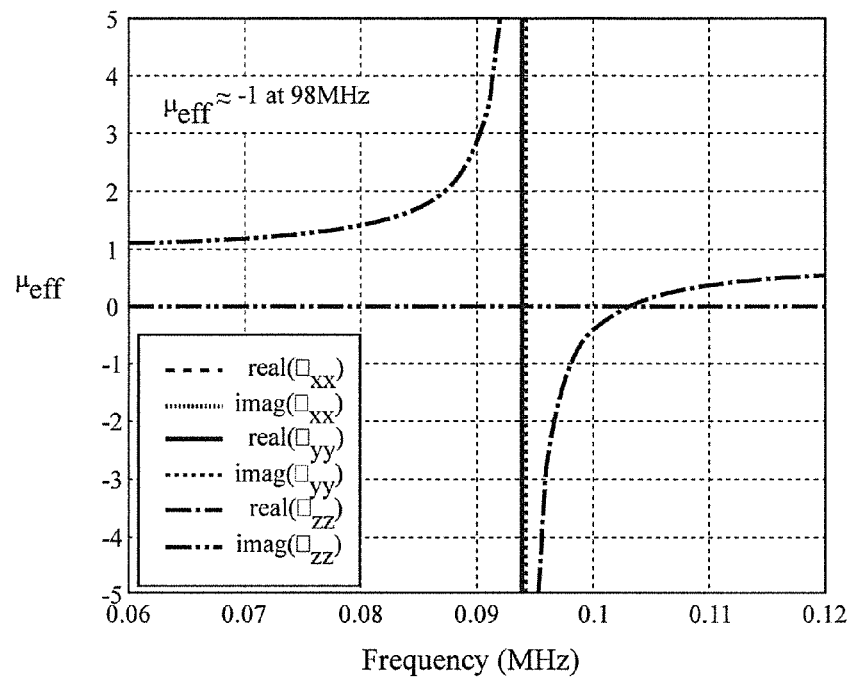

FIG. 10A-10C further illustrate the design process, adding four vertical SRRs identical to the top and bottom ones discussed in relation to FIGS. 9A-9D. The resonators have a pair of ring structures, 200 and 202, each with a gap across which a lumped capacitor is mounted. The isotropic unit cell design has the following parameters: unit cell size of 8.35 mm×8.35 mm×8.35 mm; dielectric thickness of 0.254 mm; dielectric material is Rogers RO3035; SRRs are printed on the inner faces of the dielectric; lumped capacitors are 120 pF.

FIG. 10A shows the configuration of the split ring resonators (SRRs), including ring structures 200 and 202. FIG. 10B shows the locations 204 of lumped elements, in this example surface mount capacitors. FIG. 10C shows the frequency response of a metamaterial using this unit cell configuration. Here, $\mu_{eff}=-1$ at 98 MHz.

In a useful simplification, the dielectric layers may be omitted from the simulations. Without the dielectric slabs, the resonant frequency changes very little (possibly a 1-2% change in the $\mu_{eff}=-1$ frequency may be observed). Therefore, the simplified structure may be used in finite array simulations. Adding another metamaterial layer to the simulated structure, the $\mu_{eff}=-1$ band does not shift. The retrieved $\mu_{eff}$ for one layer approaches that of a bulk metamaterial with a plurality of layers.

Figure 11:
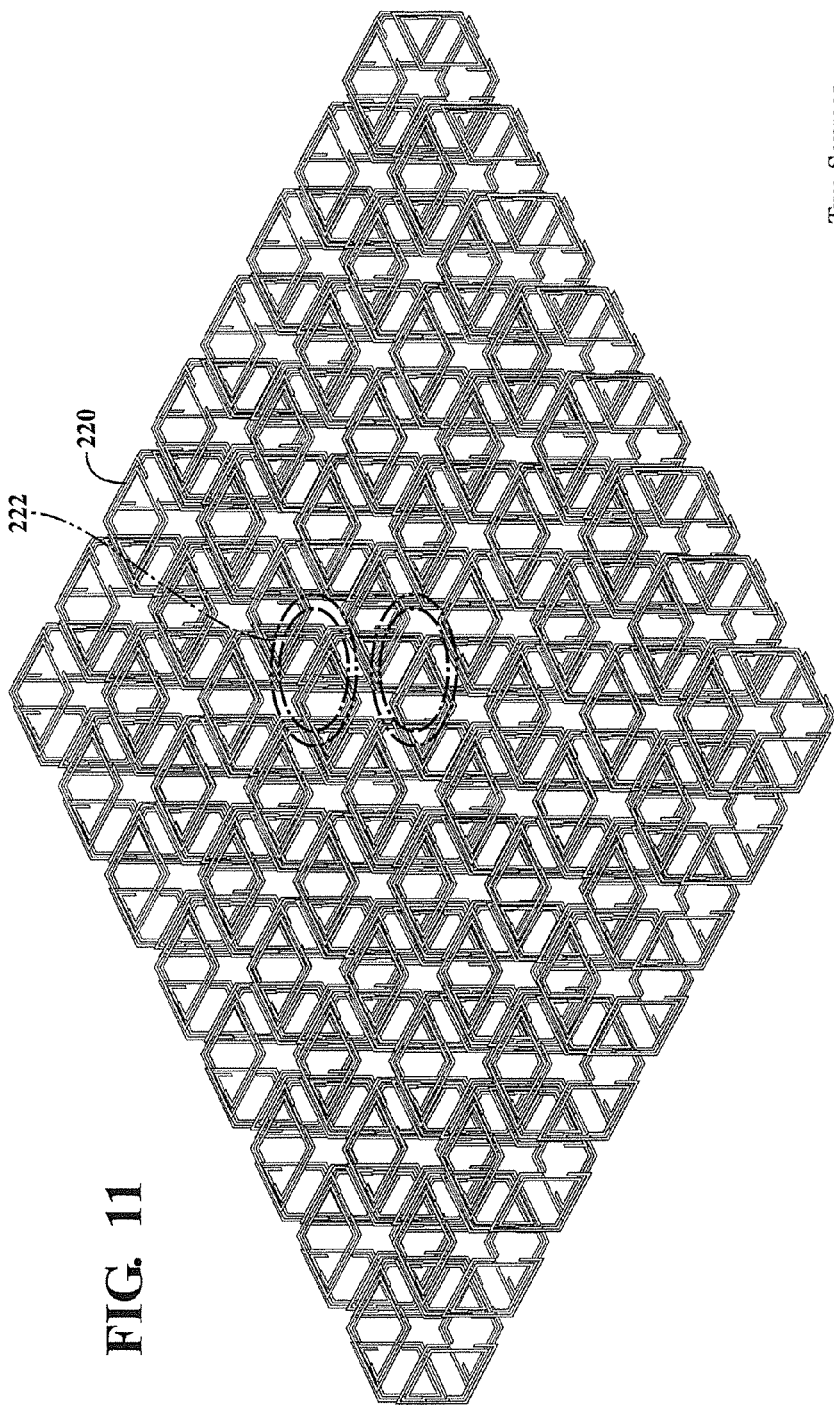
FIG. 11 shows an isotropic metamaterial lens.

FIG. 11 shows an example structure used in an isotropic metamaterial lens simulation, using a full-wave finite array simulation in HFSS, showing two loop sources (e.g. 222) on one side of the simulated lens 220.

Figure 12E:
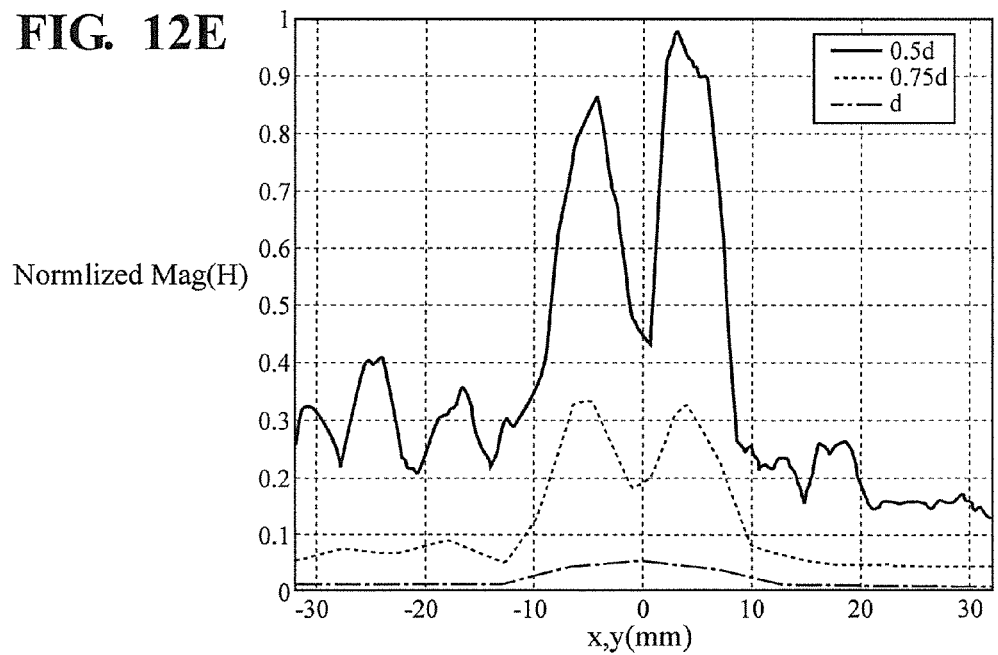
FIGS. 12A-12F illustrate simulation results for an isotropic metamaterial lens.
Figure 12A:
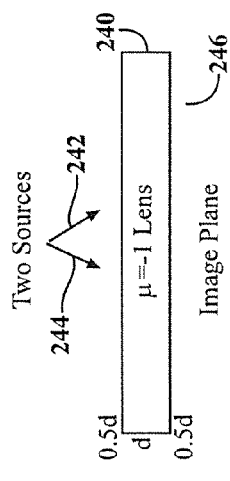
Figure 12B:
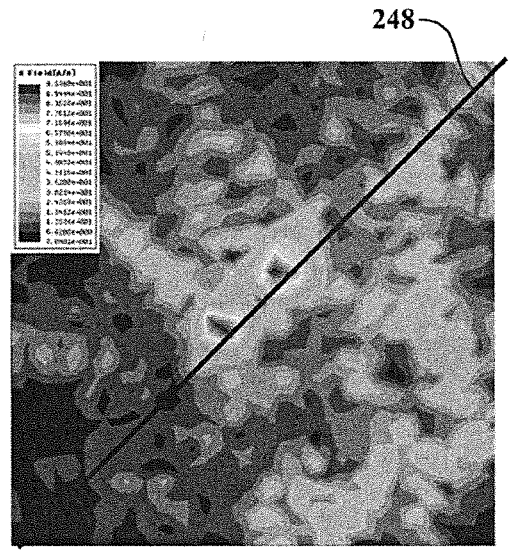
Figure 12C:
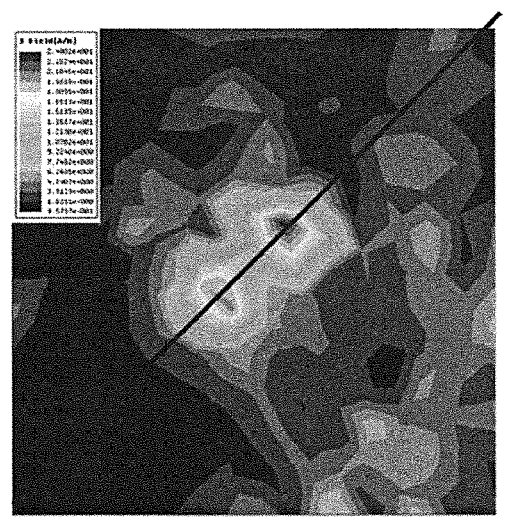
Figure 12D:
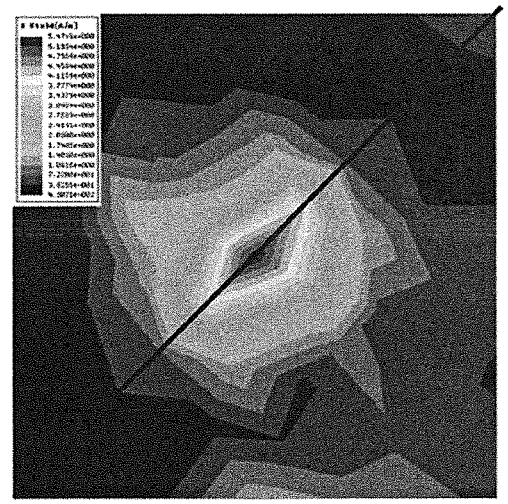

FIGS. 12A-12F illustrate simulation results for an isotropic metamaterial lens, such as shown in FIG. 11. An isotropic lens may be modeled as a homogenous slab 240 with $\mu=-1$ (i.e. as an ideal lens). In this approach, the effective permeability retrieved from one unit cell is assigned to the homogeneous slab. FIG. 12A shows two sources 242 and 244) located on one side of the lens, with an image plane 246 located on the other side of the lens 240. FIGS. 12B-12D show images of field distributions at different image plane separations from the lens, as also shown in FIG. 12E. The lines, such as 248 in FIG. 12B, shows the location of the cross-section plots of FIG. 12E.

Figure 12F:
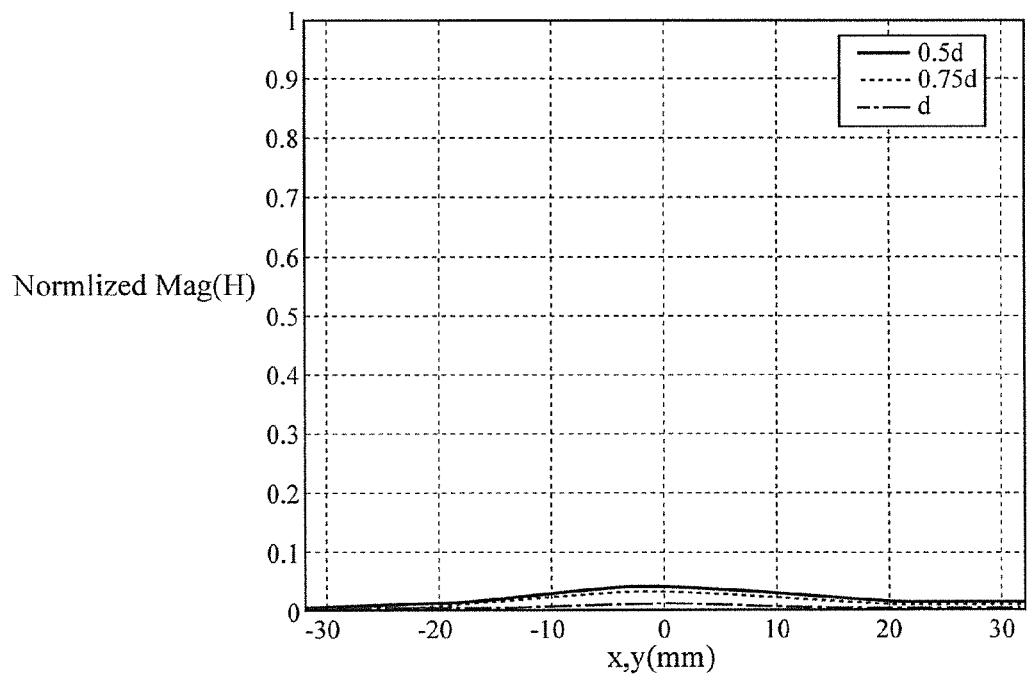

For comparison, FIG. 12F shows results also obtained without an isotropic metamaterial lens, where the free space permeability is assigned to the homogeneous slab. This shows that the two magnetic sources cannot be resolved without the metamaterial lens (i.e. in free space alone).

Figure 13A:
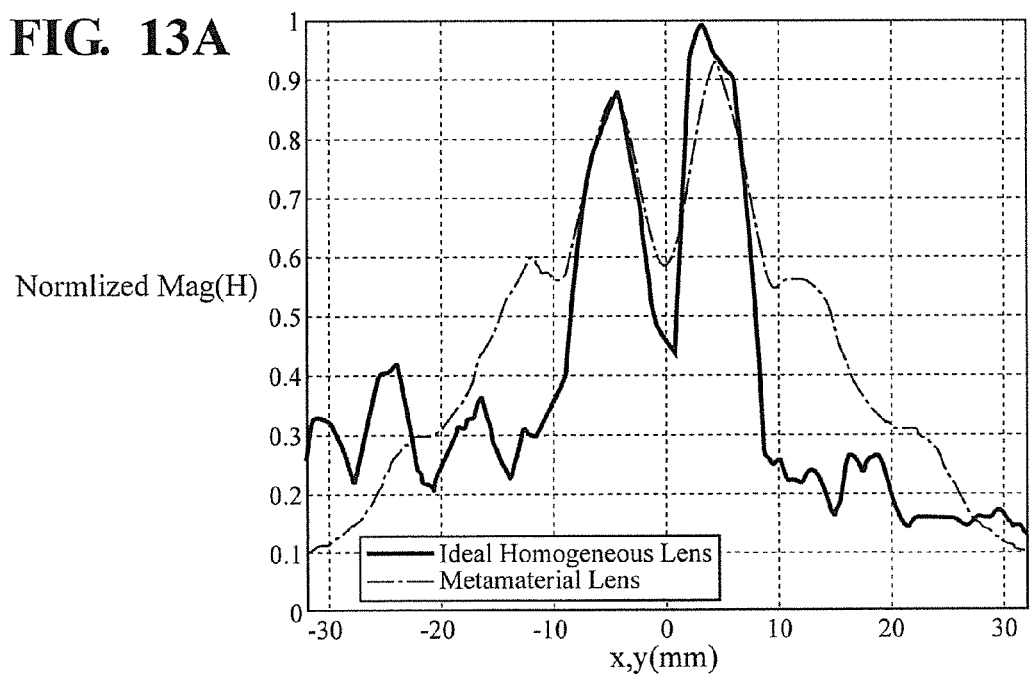
FIG. 13A-13C indicates that the isotropic nature of the lens produces images with sub-wavelength resolution.
Figure 13B:
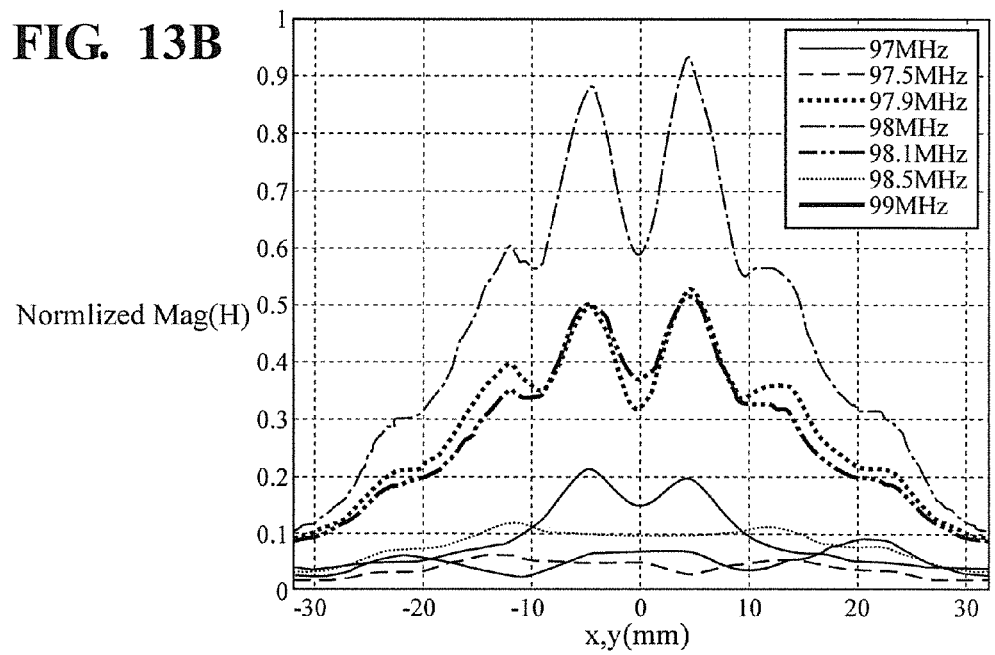
Figure 13C:
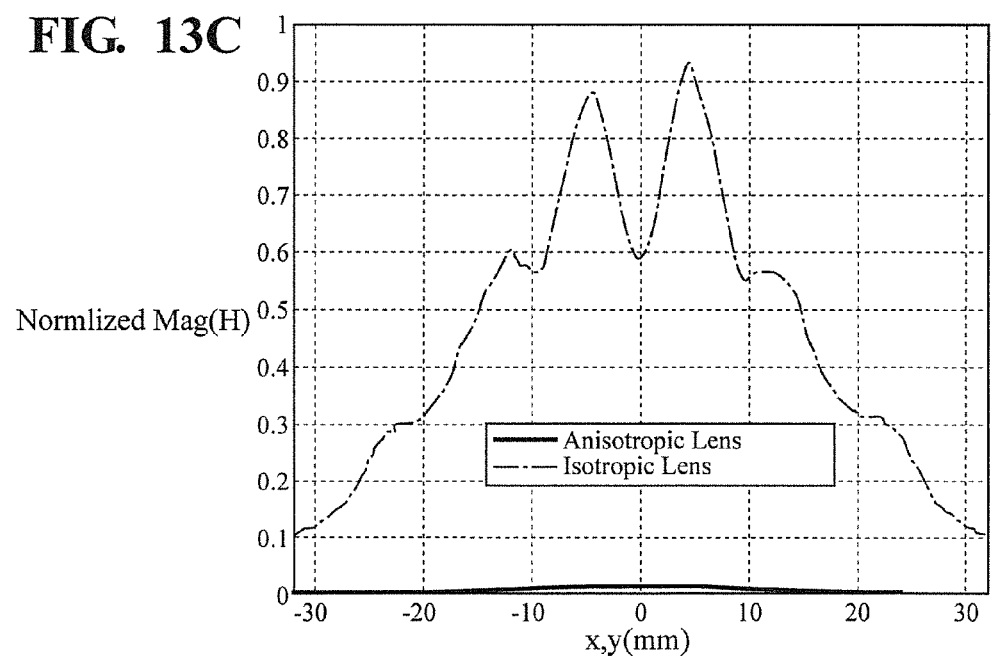

FIGS. 13A-13C further illustrate isotropic metamaterial lens bandwidth and responsivity. The simulated results show excellent performance for a finite metamaterial lens, 8 by 8 unit cells, with two loop sources at r=5 mm and an image plane 0.5 d away from the lens. FIG. 13A is a comparison between an ideal (homogenous) lens and the actual simulated isotropic lens with 8×8 unit cells). The ideal lens is a good approximation of the actual lens.

FIG. 13B shows the image plane normalized magnetic field as a function of frequency.

FIG. 13C shows a comparison of simulation results for lenses with (i.e. isotropic lens) and without vertical SRRs. These results demonstrate that the focusing effect of the lens is provided by the isotropic $\mu_{eff}$, and it is indeed the isotropy that produces the image with sub-wavelength resolution and large detection depth. A finite isotropic lens can resolve the two sources and performs quite similarly to the ideal homogeneous lens. The operational bandwidth of the lens is ~20 kHz.

Further Discussion of Applications

Examples of the present invention include MRI apparatus including metamaterial lenses described herein. An apparatus may include a magnet, such as a superconducting magnet, to provide the magnetic field, which may be in the range 0.1-20 T, for example. Further components, known in the art, may include field gradient coils, transmitter coils, receiver coils, and data analysis circuitry operable to construct an image from received signals. A metamaterial may be a generally planar structure, for example a two-dimensional repeated array of unit cell structures. However, generally planar structures may also be multilayer structures.

Applications include any magnetic resonance apparatus, including MRI apparatus, NMR spectrometers, NQR apparatus, any apparatus configured to detect specific nuclei within a sample, radio-frequency (rf) detection apparatus, radio-frequency antennas or receivers, or any apparatus for conditioning transmitted and/or detected electromagnetic radiation. Applications further include any radiofrequency apparatus for which focusing or other manipulation of an rf field is obtained using a metamaterial such as described herein, including non-destructive testing, imaging, spectroscopy, concealed object detection, and the like. In some examples, metamaterial lenses may also be dynamically variable or include one or more gradient properties, for example using tunable dielectric materials. In some examples, resonator parameters may be varied as a function of position along one or more directions, to obtain a gradient index metamaterial lens.

Any suitable low-loss dielectric substrate may be used, such as orthogonal planar substrates or other configuration. In some examples, conducting element structures may be at least partially self-supporting. Features may be printed or supported on one or both sides of a dielectric substrate.

The invention is not restricted to the illustrative examples described above. Examples described are not intended to limit the scope of the invention. Changes therein, other combinations of elements, and other uses will occur to those skilled in the art.

Having described our invention, we claim:

1. A metamaterial lens having an operating frequency comprising:
   a plurality of dielectric substrates arranged in the form of a plurality of unit cells;
   the metamaterial lens having an isotropic magnetic permeability of $\mu=-1$ at an operating frequency;
   the metamaterial lens including resonators arrayed in three orthogonal planes, each of said resonators on one of said dielectric substrates,
   each resonator including a conducting ring structure and a surface-mounted reactive component.

2. The lens of claim 1, the metamaterial lens wherein said dielectric substrates are arranged in three orthogonal planes,
   the resonators being ring resonators formed by conducting patterns located on the dielectric substrates,
   the surface-mounted reactive components being mounted on the conducting patterns across gaps therein.

3. The lens of claim 1, the metamaterial lens having a repeated unit cell structure,
   each unit cell being a cubic unit cell with resonators located at each face thereof.

4. The lens of claim 1, each resonator including a surface-mounted capacitor.

5. The lens of claim 1, each resonator including a surface-mounted inductor.

6. The lens of claim 1, each resonator including a surface-mounted inductor and a surface-mounted capacitor.

7. The lens of claim 1, each resonator including a meander-line inductor and a surface-mounted capacitor.

8. The lens of claim 1 physically associated with an apparatus, the apparatus being a nuclear magnetic resonance apparatus including a magnet,
   wherein the operating frequency is a nuclear resonance frequency in the nuclear magnetic resonance apparatus.

9. The lens of claim 8, the nuclear magnetic resonance apparatus being a magnetic resonance imaging apparatus.

10. The lens of claim 1, wherein the image resolution of the metamaterial lens is smaller than $\lambda/100$, where $\lambda$ is the electromagnetic wavelength at the operating frequency.

11. The lens of claim 1, wherein said dielectric substrates are arranged in three dimensions to form cubic structures, there being a resonator located at each face of the cubic structure.

12. The lens of claim 1, the wherein the operating frequency is a nuclear resonance frequency within an imaged object.

13. The lens of claim 1, wherein the operating frequency is in the range 1 MHz to 1 GHz.

14. The lens of claim 1, wherein the operating frequency is in the range 5 MHz to 500 MHz.

15. A method of increasing MRI resolution of an imaged object in an MRI apparatus having a magnet and an imaging sensor, without increasing a magnetic field strength of the magnet, the method including:

introducing the metamaterial lens of claim 1 to the MRI apparatus between the imaged object and an imaging sensor, thereby increasing the MRI resolution.

16. A metamaterial lens having an operating frequency between 1 MHz and 1 GHz, said lens comprising,
   a plurality of dielectric substrates arranged in the form of a plurality of unit cells;
   the metamaterial lens having an isotropic magnetic permeability of −1 at the operating frequency,
   the each of said dielectric substrates including a resonator, said resonator including a conducting ring structure having a gap therein and a reactive component electrically connected across the gap.

17. The apparatus of claim 16, the metamaterial wherein said dielectric substrates are arranged parallel to three orthogonal planes and intersecting so as to form dielectric cubes, the resonators being located on faces of the dielectric cubes.

* * * * *